United States Patent
Turos et al.

(10) Patent No.: US 11,116,725 B2
(45) Date of Patent: Sep. 14, 2021

(54) NANOPARTICLES CARRYING ANTIBIOTICS

(71) Applicant: UNIVERSITY OF SOUTH FLORIDA, Tampa, FL (US)

(72) Inventors: Edward Turos, Wesley Chapel, FL (US); Faeez Mahzamani, Brandon, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 49 days.

(21) Appl. No.: 16/183,068

(22) Filed: Nov. 7, 2018

(65) Prior Publication Data

US 2019/0133944 A1 May 9, 2019

Related U.S. Application Data

(60) Provisional application No. 62/583,209, filed on Nov. 8, 2017.

(51) Int. Cl.
| | | |
|---|---|---|
| *A61K 9/14* | (2006.01) | |
| *A61K 9/107* | (2006.01) | |
| *A61P 31/04* | (2006.01) | |
| *A61K 47/58* | (2017.01) | |
| *A61K 31/496* | (2006.01) | |
| *A61K 47/20* | (2006.01) | |
| *A61K 47/55* | (2017.01) | |
| *A61K 47/69* | (2017.01) | |

(52) U.S. Cl.
CPC .......... *A61K 9/1075* (2013.01); *A61K 31/496* (2013.01); *A61K 47/20* (2013.01); *A61K 47/552* (2017.08); *A61K 47/58* (2017.08); *A61K 47/6907* (2017.08); *A61P 31/04* (2018.01)

(58) Field of Classification Search
None
See application file for complete search history.

(56) References Cited

U.S. PATENT DOCUMENTS

2007/0190160 A1* 8/2007 Turos .................. A61K 9/5138
424/490

OTHER PUBLICATIONS

Abeylath, S. C. et al., "Nanobiotics to Combat Bacterial Drug Resistance," *Antibiotic Resistance*, 2009, pp. 1-43, Nova Science Publishers, Inc.

Abeylath, S. C. et al., "Glycosylated polyacrylate nanoparticles by emulsion polymerization," *Carbohydrate Polymers*, 2007, 70:32-37, Elsevier Ltd.

Abeylath, S. C. et al., "Glyconanobiotics: Novel carbohydrated nanoparticle antibiotics for MRSA and Bacillus anthracis," *Bioorganic & Medicinal Chemistry*, 2008, 16:2412-2418, Elsevier Ltd.

Alonso, M. J. et al., "Joint effects of monomer and stabilizer concentrations on physico-chemical characteristics of poly(butyl 2-cyanoracrylate) nanoparticles," *J. Microencapulation*, 1990, 7(4):517-526, Taylor & Francis Ltd.

An, B. et al., "Enhanced Emission and Its Switching in Fluorescent Organic Nanoparticles," *J. Am. Chem. Soc.*, 2002, 124:14410-14415, American Chemical Society.

Azéma, J. et al., "7-((4-Substituted)piperazin-1-yl) derivatives of ciprofloxacin: Synthesis and in vitro biological evaluation as potential antitumor agents," *Bioorganic & Medicinal Chemistry*, 2009, 17:5396-5407, Elsevier Ltd.

Bankova, M. et al., "Hydrolysis and Antibacterial Activity of Polymers Containing 8-Quinolinyl Acrylate," *Journal of Bioactive and Compatible Polymers*, Oct. 1997, 12:294-307, Technomic Publishing Co., Inc.

Benson, H. A. et al., "Influence of anatomical site and topical formulation on skin penetration of sunscreens," *Therapeutics and Clinical Risk Management*, 2005, 1(3):209-218, Dove Medical Press Limited.

Bieri, M. et al., "Probing chiral interfaces by infrared spectroscopic methods," *Physical Chemistry Chemical Physics*, 2007, 9:671-685.

Boudad, H. et al., "Combined hydroxypropyl-ß-cyclodxtrin and poly(alkylcyanoacrylate) nanoparticles intended for oral administration of saquinavir," *International Journal of Pharmaceutics*, 2001, 218:113-124, Elsevier Science B. V.

Calvo, P. et al., "Chitosan and Chitosan/Ethylene Oxide-Propylene Oxide Block Copolymer Nanoparticles as Novel Carriers for Proteins and Vaccines," *Pharmaceutical Research*, 1997, 14(10):1-7.

Calvo, P. et al., "Novel Hydrophilic Chitosan-Polyethylene Oxide Nanoparticles as Protein Carriers," *Journal of Applied Polymer Science*, 1997, 63:125-132, John Wiley & Sons, Inc.

(Continued)

Primary Examiner — Jessica Worsham
(74) Attorney, Agent, or Firm — Quarles & Brady LLP

(57) ABSTRACT

The subject invention pertains to polyacrylate homopolymers produced from acrylolated drug monomers. The homopolymers can be produced in the form of nanoparticles. The nanoparticles comprising the homopolymers can be produced via a free radical-induced emulsion polymerization of the acrylolated drug monomers to produce an aqueous emulsion of uniformly sized nanoparticles. The homopolymers of the invention containing acrylolated antibiotic monomers can be active against Gram-positive and Gram-negative bacteria, such as *Staphylococcus aureus* and *Escherichia coil*. Accordingly, methods are provided of treating a disease, for example, an infection, by administering to a subject the homopolymers, homopolymeric nanoparticles, or emulsions containing homopolymeric nanoparticles of the invention.

7 Claims, 6 Drawing Sheets

(56) References Cited

OTHER PUBLICATIONS

Campieri, M et al., "Bacteria as the cause of ulcerative colitis," *Gut*, 2001, 48:132-135.
Cavallaro, G. et al., "Entrapment of ß-lactams antibiotics in polyethylcyanoacrylate nanoparticles: Studies on the possible in vivo application of this colloidal delivery system," *International Journal of Pharmaceutics*, 1994, 111:31-41, Elsevier Science B. V.
Cormier, R. et al., "Studies on the antimicrobial properties of N-acylated ciprofloxacins," *Bioorganic & Medicinal Chemistry Letters*, 2012, 22:6513-6520, Elsevier Ltd.
Couvreur, P. et al., "Polycyanoacrylate nanocapsules as potential lysosomotropic carriers: preparation, morphological and sorptive properties," *Journal of Pharmacy and Pharmacology*, 1979, 31(5):331-332.
Fawaz, F. et al., "Ciproflexacin-loaded polyisobutylcyanoacrylate nanoparticles: preparation and characterization," *International Journal of Pharmaceutics*, 1997, 154:191-203, Elsevier Science B. V.
Fontana, G. et al., "Amoxicillin-loaded polyethylcyanoacrylate nanoparticles: Influence of PEG coating on the particle size, drug release rate and phagocytic uptake," *Biomaterials*, 2001, 22:2857-2865, Elsevier Science B. V. Ltd.
Fu, H. et al., "Multiple Emissions from 1,3-Diphenyl-5-pyrenyl-2-pyrazoline Nanoparticles: Evolution from Molecular to Nanoscale to Bulk Materials," *Angew. Chem. Int. Ed.*, 2002, 41(6):962-965, WILEY-VCH.
Garay-Jimenez, J. C. et al., "Physical properties and biological activity of poly(butyl acrylate-styrene) nanoparticle emulsions prepared with conventional and polymerizable surfactants," *Nanomedicine: Nanotechnology, Biology, and Medicine*, 2009, 5:443-451, Elsevier Inc.
Garay-Jimenez, J. C. et al., "A convenient method of prepare emulsified polyacrylate nanoparticles from for drug delivery applications," *Bioorganic & Medicinal Chemistry Letters*, 2011, 21:4589-4591, Elsevier Ltd.
Geier, M. S. et al., "Inflammatory bowel disease: Current insights into pathogenesis and new therapeutic options; probiotics, prebiotics and synbiotics," *International Journal of Food Microbiology*, 2007, 115:1-11, Elsevier B. V.
Greenhalgh, K. et al., "In vivo studies of polyacrylate nanoparticle emulsions for topical and systemic applications," *Nanomedicine: Nanotechnology, Biology, and Medicine*, 2009, 5:46-54, Elsevier Inc.
Gu, H. et al., "Presenting Vancomycin on Nanoparticles to Enhance Antimicrobial Activities," *Nano Letters*, 2003, 3(9):1261-1263, American Chemical Society.
Guo, Z. et al., "Enantioselectively controlled release of chiral drug (metoprolol) using chiral mesoporous silica materials," *Nanotechnology*, 2010, 21:1-12, IOP Publishing Ltd.
Hanauer, S. B., "New lessons: classic treatments, expanding options in ulcerative colitis," *Colorectal Disease*, 2006, 8:20-24, Blackwell Publishing Ltd.
Hanley, C. et al., "The Influences of Cell Type and ZnO Nanoparticle Size on Immune Cell Cytotoxicity and Cytokine Induction," *Nanoscale Res. Letters*, 2009, 4:1409-1420.
Hasan, S., "A Review on Nanoparticles: Their Synthesis and Types," *Research Journal of Recent Sciences*, 2015, 4:9-11.
Hue, S. et al., "Interleukin-23 drives innate and T cell-mediated intestinal inflammation," *JEM*, Oct. 30, 2006, 203(11):2473-2483, The Rockefeller University Press.
Kanazawa, A. et al., "Antibacterial Activity of Polymeric Sulfonium Salts," *Journal of Polymer Science: Part A: Polymer Chemistry*, 1993, 31:2873-2876, John Wiley & Sons, Inc.
Kisich, K. O. et al., "Encapsulation of moxifloxacin within poly(butyl cyanoacrylate) nanoparticles enhances efficacy against intracellular *Mycobacterium tuberculosis*," *International Journal of Pharmaceutics*, 2007, 345:154-162, Elsevier B. V.
Klotz, U. et al., "Pharmacology and Pharmacokinetics of 5-Aminosalicylic Acid," *Digestive Diseases and Sciences*, Dec. 1987, 32(12):465-505, Plenum Publishing Corporation.
Kommareddy, S. et at., "Poly(ethylene glycol)-modified thiolated gelatin nanoparticles for glutathione-responsive intracellular DNA delivery," *Nanomedicine: Nanotechnology, Biology, and Medicine*, 2007, 3:32-42, Elsevier Inc.
Kwon, H. et al., "Preparation of PLGA nanoparticles containing estrogen by emulsification-diffusion method," *A: Physicochemical and Engineering Aspects*, 2001, 182:123-130, Elsevier Science B. V.
Labruère, R. et al., "Attenuating the size and molecular carrier capabilities of polyacrylate nanoparticles by a hydrophobic fluorine effect," *Bioorganic & Medicinal Chemistry*, 2012, 20, 5042-5045, Elsevier Ltd.
Li, J. et al., "Biomimetic synthesized chiral mesoporous silica: Structures and controlled release functions as drug carrier," *Materials Science and Engineering*, 2015, 55:367-372, Elsevier B. V.
Mayer, C., "Nanocapsules as drug delivery systems," *The International Journal of Artificial Organs*, 2005, 28(11):1163-1171, Wichtig Editore.
Moon, W. et al., "Antimicrobial Effect of Monomers and Polymers with Azole Moieties," *Journal of Applied Polymer Science*, 2003, 90:2933-2937, Wiley Periodicals, Inc.
Moon, W. et al., "Antimicrobial Activity of a Monomer and Its Polymer Based on Quinolone," *Journal of Applied Polymer Science*, 2003, 90:1797-1801, Wiley Periodicals, Inc.
Nonaka, T. et al., "Synthesis of Water-Soluble Thermosensitive Polymers Having Phosphonium Groups from Methacryloyloxyethyl Trialkyl Phosphonium Chlorides-N-Isopropylacrylamide Copolymers and Their Functions," *Journal of Applied Polymer Science*, 2003, 87:386-393, Wiley Periodicals, Inc.
Oh, S. T. et al., "Synthesis and Biocidal Activites of Polymer. III. Bactericidal Activity of Homopolymer of AcDP and Copolymer of AcDP with St.," *Journal of Applied Polymer Science*, 1994, 54:859-866, John Wiley & Sons, Inc.
Podolsky, D. K., "Inflammatory Bowel Disease," *N Engl J Med.*, 1991, 325(13):928-937.
Puglisi, G. et al., "Influence of the preparation conditions on poly(ethylcyanoacrylate) nanocapsule formation," *International Journal of Pharmaceutics*, 1995, 125:283-287, Elsevier Science B. V.
Qiu, X. et al., "Origin of the Enhanced Photocatalytic Activities of Semiconductors: A Case Study of ZnO Doped with $Mg^{2+}$," *J. Phys. Chem. C*, 2008, 112:12242-12248, American Chemical Society.
Rousseaux, C. et al., "Intestinal anti-inflammatory effect of 5-aminosalicylic acid is dependent on peroxisome proliferator-activated receptor-γ," *JEM*, Apr. 18, 2005, 201(8):1205-1215, The Rockefeller University Press.
Santos-Magalhães, N. S. et al., "Colloidal carriers for benzathine penicillin G: Nanoemulsions and nanocapsules," *International Journal of Pharmaceutics*, 2000, 208:71-80, Elsevier Science B. V.
Seijo, B. et al., "Design of nanoparticles of less than 50 nm diameter: preparation, characterization and drug loading," *International Journal of Pharmaceutics*, 1990, 62:1-7, Elsevier Science Publishers B. V.
Suksuwan, A. et al., "The composite nanomaterials containing (R)-thalidomine-molecularly imprinted polymers as a recognition system for enantioselective-controlled release and targeted drug delivery," *Journal of Applied Polymer Science*, 2015, 132:1-21, Wiley Periodicals, Inc.
Taylor, R. et al., "Nanofluid-based optical filter optimization for PV/T systems," *Light: Science& Applications*, 2012, 1:1-7, CIOMP.
Thamizharasi, S. et al., "Synthesis, characterization and pharmacologically active sulfamethoxazole polymers," *European Polymer Journal*, 2002, 38:551-559, Elsevier Science Ltd.
Tom, R. T. et al., "Ciprofloxacin-Protected Gold Nanoparticles," *Langmuir*, 2004, 20:1909-1914, American Chemical Society.
Turos, E. et al., "Penicillin-bound polyacrylate nanoparticles: Restoring the activity of ß-lactam antibiotics against MRSA," *Bioorganic & Medicinal Chemistry Letters*, 2007, 17:3468-3472, Elsevier Ltd.
Turos, E. et al., "Antibiotic-Conjugated Polyacrylate Nanoparticles: New Opportunities for Development of Anti-MRSA Agents," *Bioorg Med Chem Lett*, Jan. 1, 2007, 17(1):53-56.

(56) References Cited

OTHER PUBLICATIONS

Uemura, Y. et al., "Preparation of Resins Having Various Phosphonium Groups and Their Adsorption and Elution Behavior for Anionic Surfactants," *Journal of Applied Polymer Sciences*, 1999, 72:371-378, John Wiley & Sons, Inc.

Wang, Y. et al., "Intercalation of $_L$-Alanyl-Glutamine Dipepitde into Layered Double Hydroxides: Configuration Stabilization in Confined Interlayer Region," *Ind. Eng. Chem. Res.*, 2012, 51:11128-11136, American Chemical Society.

Yang, S. et al., "On the Origin of Helical Mesostructures," *J. Am. Chem. Soc.*, 2006, 128:10460-10466, American Chemical Society.

You, C. et al., "Isomeric Control of Protein Recognition with Amino Acid- and Dipepetide-Functionalized Gold Nanoparticles," *Chem. Eur. J.*, 2008, 14:143-150, Wiley-VCH.

Youssef, M. et al., "Effectiveness of Nanoparticle-Bound Ampicillin in the Treatment of *Listeria monocytogenes* Infection in Athymic Nude Mice," *Antimicrobial Agents and Chemotherapy*, Aug. 1988, 32(8):1204-1207, American Society for Microbiology.

Zambaux, M. F. et al., "Influence of experimental parameters on the characteristics of poly(lactic acid) nanoparticles prepared by a double emulsion method," *Journal of Controlled Release*, 1998, 50:31-40, Elsevier Science B. V.

Iwakura, Y. et al., "Synthesis and Polymerization of N-[(1-Substituted-2-oxopropyl)]acrylamides and-methacrylamides. Copolymerization of These Monomers with Styrene and Substituent Effects," *Journal of Polymer Science, Part A-I*, 1967, 5:1599-1607.

\* cited by examiner

Compound 9

NANOPARTICLES CARRYING ANTIBIOTICS

CROSS-REFERENCE TO RELATED APPLICATION

This application claims the benefit of U.S. Provisional Application No. 62/583,209, filed Nov. 8, 2017, the disclosure of which is hereby incorporated by reference in its entirety including any tables, figures, or drawings.

BACKGROUND OF THE INVENTION

The growing antibiotic resistance of harmful microbes, such as methicillin-resistant *Staphylococcus aureus* (MRSA), has emerged as one of the dominating concerns of today's public health system, causing scientists to look for ways to circumvent this resistance through drug delivery methods and systems.

Aqueous polyacrylate nanoparticle emulsions for the purpose of water-solubilizing and encasing certain antibacterial compounds were described as means to improve their stability and antibiotic activity especially towards multi-drug resistant strains of bacteria. These nanoparticle emulsions were prepared through radical-induced emulsion polymerization of butyl acrylate/styrene mixtures (7:3 w/w) in water at 600° C., using sodium dodecyl sulfate (SDS) as an emulsifying agent and potassium persulfate as a radical initiator. The reactions led to the formation of homogeneous, stable aqueous emulsions containing uniformly-sized nanoparticles of 45-50 nm in diameter. The method was successfully applied to penicillins and N-thiolated β-lactams, such that the antibacterial agents could be introduced into the nanoparticle either by non-covalent entrapment as a free drug, or covalently via an acryloyl derivative. The antibiotic-containing nanoparticles showed promising in vitro activity against pathogenic bacteria such as methicillin-resistant *S. aureus* (MRSA).

While these earlier nanoparticle emulsions provided increased water solubility and, in some cases, improved bioactivity of the β-lactam antibacterial agent, the polyacrylate backbone was largely comprised of non-bioactive monomers (butyl acrylate-styrene or methyl methacrylate-styrene), and only 1-3% (by weight) of the antibacterial agent in the nanoparticle. The amount of drug loading into the nanoparticle during the assembly process was limited by how much surfactant could be used, given that amounts exceeding 3% (by weight) of SDS caused discernable cytotoxicity. These emulsions contained up to 20% of solid content (as a mixture of nanoparticles and a small amount of non-emulsified polymers) and 0.2-1% of the antibacterial agent inside of the nanoparticles. The resulting emulsions were typically milky in consistency and somewhat sticky when exposed to air, causing films to rapidly form when dried. Also, unwanted coagulation within syringes, microporous filters, and gel columns made it very difficult to purify and use them for in vivo testing. Purification techniques that enable the removal of residual unreacted monomers and non-nanoparticle oligomers within the emulsion could address some of these issues. Therefore, polymeric nanoparticles that are soluble in water and contain higher amount of drugs are desirable.

BRIEF SUMMARY OF THE INVENTION

This disclosure describes polymers produced from acrylate monomers of drugs, particularly, polymers produced exclusively from acrylate monomers of drugs, and surfactant combinations. The polymers disclosed herein contain higher amounts of drugs without increasing overall cytotoxicity or instability of the emulsion.

Certain embodiments of the invention provide methods of preparing nanoparticle emulsions containing an acrylated drug as the sole monomer for producing polymeric nanoparticle emulsion. In preferred embodiments, the drug can be chemically modified to connect an acrylate group to the drug, i.e., acrylolated. In even more preferred embodiments, the drug is an antibiotic, for example, ciprofloxacin.

Further embodiments of the invention provide methods of producing polymeric nanoparticle emulsions containing an acrylolated drug as the sole monomer for producing the polymeric nanoparticle emulsion. Certain such methods comprise pre-solubilization of a water-insoluble drug, for example, an antibacterial agent, in an organic solvent to permit more uniform addition into the aqueous solution and to form homogeneous emulsions. In preferred embodiments, dichloromethane is used to solubilize the monomeric acrylolated drug, e.g., monomeric acrylolated ciprofloxacin.

In additional embodiments, increased temperature of about 90° C. (rather than 75° C.) for polymerization, increased stir speed of about 1100 rpm (rather than 750 rpm), and the addition of a surfactant, such as sodium dodecyl sulfate, before adding the monomers can be performed to further facilitate evaporation of an organic solvent. In further embodiments, the polymerization reactions are run for about 48 hours (rather than the usual 6 hours).

Further embodiments of the invention provide methods of treating a disease in a subject, for example, an infection, by administering to the subject the homopolymers of acrylolated drugs, nanoparticles comprising the homopolymers of acrylolated drugs, or emulsions containing the nanoparticles of the homopolymers of the acrylolated drugs of the invention.

DETAILED DISCLOSURE OF THE INVENTION

Figure 1:
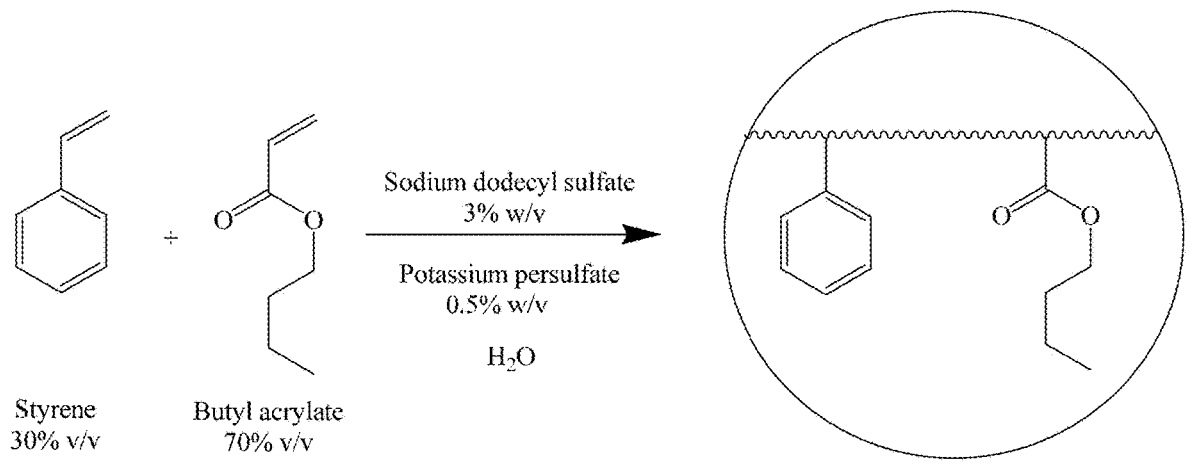
FIG. 1. Scheme for preparing poly(acrylate-styrene) emulsions.
Figure 2:
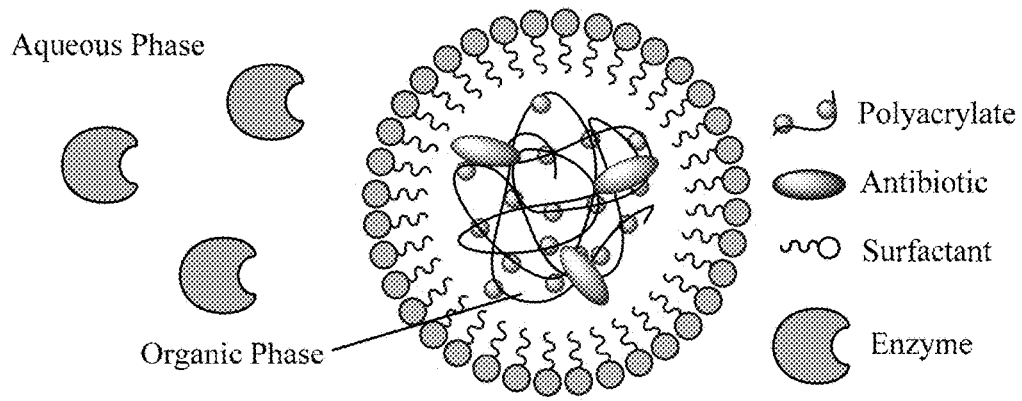
FIG. 2. Co-monomer-based encapsulation of antibiotic into polyacrylate nanoparticle emulsions.
Figure 3:
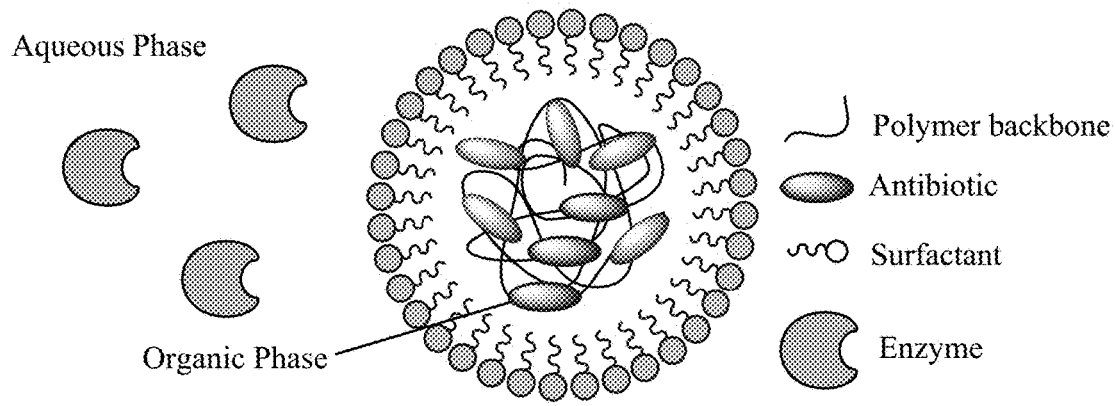
FIG. 3. Removal of co-monomers and formation of polymer via 100% of the acrylate antibiotic analog.
Figure 4:
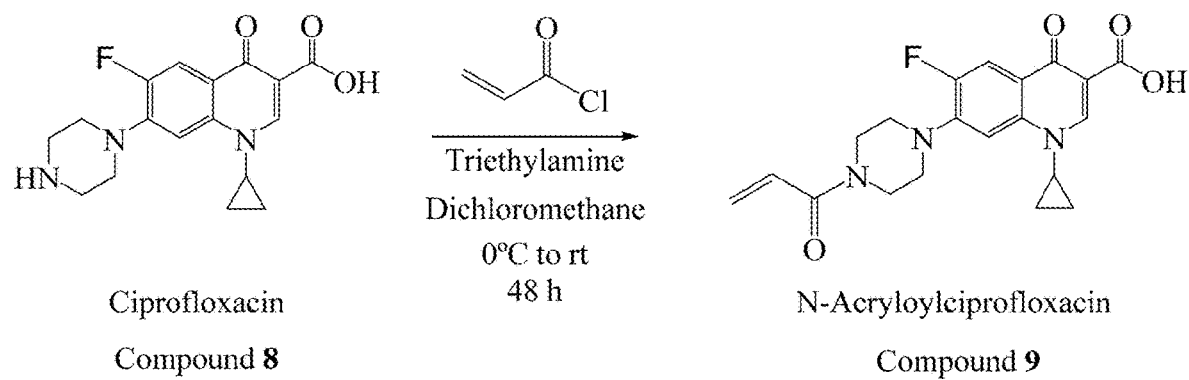
FIG. 4. Scheme for synthesis of N-acryloylciprofloxacin.

As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof) "comprising," "comprises,"

"comprise," "consisting essentially of," "consists essentially of," "consisting," and "consists" can be used interchangeably.

The phrases "consisting essentially of" or "consists essentially of" indicate that the claim encompasses embodiments containing the specified materials or steps and those that do not materially affect the basic and novel characteristic(s) of the claim.

The term "about" means within an acceptable error range for the particular value as determined by one of ordinary skill in the art, which will depend in part on how the value is measured or determined, i.e., the limitations of the measurement system. For example, where the term "about" is used to describe compositions containing amounts of ingredients or a temperature or a rate of stirring, these parameters can be varied between 0% and 10% around the stated value (X±10%).

In the present disclosure, ranges are stated in shorthand, so as to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc. Values having at least two significant digits within a range are envisioned, for example, a range of 5-10 indicates all the values between 5.0 and 10.0 as well as between 5.00 and 10.00 including the terminal values. When ranges are used herein combinations and subcombinations of ranges (e.g., subranges within the disclosed range) and specific embodiments therein are intended to be explicitly included.

"Pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the antigen in the vaccine, its use in the vaccine compositions of the invention is contemplated.

"Treatment" (and grammatical variants of these terms), as used herein, are used interchangeably. These terms refer to an approach for obtaining beneficial or desired results including but not limited to therapeutic benefit. A therapeutic benefit is achieved with the eradication or amelioration of one or more of the physiological symptoms associated with the underlying disorder such that an improvement is observed in the patient, notwithstanding that the patient may still be afflicted with the underlying disorder.

The term "therapeutically effective amount" refers to that amount of a drug that is sufficient to effect the intended application including but not limited to disease treatment. The therapeutically effective amount may vary depending upon the intended application or the subject and disease condition being treated, e.g., the weight and age of the subject, the severity of the disease condition, the manner of administration and the like, which can readily be determined by one of ordinary skill in the art. The specific dose will vary depending on the particular compounds chosen, the dosing regimen to be followed, whether it is administered in combination with other compounds, timing of administration, the tissue to which it is administered, and the physical delivery system in which it is carried.

"Subject" refers to an animal, such as a mammal, for example a human. The methods described herein can be useful in both humans and non-human animals. In some embodiments, the subject is a mammal (such as an animal model of disease), and in some embodiments, the subject is a human. Typical subjects include canine, feline, porcine, bovine, equine, and primate.

A homopolymer refers to a polymer consisting of only one type of monomer. A co-polymer refers to a polymer containing more than one type of monomers.

This disclosure provides polymers and nanoparticles containing such polymers. Certain polymers disclosed herein are produced by polymerization of therapeutic monomers. The polymers and nanoparticles containing such polymers can be produced in the form of an emulsion with a surfactant, such as sodium dodecyl sulfate (SDS).

Accordingly, certain embodiments of the invention provide a homopolymer of an acrylolated drug as a monomer. Acrylolation of a drug can be performed on a suitable atom in the drug, such as, C, S, O, and N, preferably, N.

In preferred embodiments, the drug is an antibiotic, such as ciprofloxacin. The antibiotic compounds can belong to a class of penicillins, N-thiolated β-lactams, or fluoroquinolones. The β-lactam antibiotic can be a penicillin, penams, cephalosporin, monobactam, or carbapenem. Non-limiting examples of β-lactam antibiotics include benzylpenicillin, benzathine benzylpenicillin, procaine benzylpenicillin, phenoxymethylpenicillin (V), propicillin, pheneticillin, azidocillin, clometocillin, penamecillin, cloxacillin, dicloxacillin, flucloxacillin, oxacillin, nafcillin, methicillin, amoxicillin, ampicillin, pivampicillin, hetacillin, bacampicillin, metampicillin, talampicillin, epicillin, ticarcillin, carbenicillin, carindacillin, temocillin, piperacillin, azlocillin, mezlocillin, mecillinam, pivmecillinam, sulbenicillin, faropenem, ritipenem, ertapenem, antipseudomonal, doripenem, imipenem, meropenem, biapenem, panipenem, cefazolin, cefalexin, cefadroxil, cefapirin, cefazedone, cefazaflur, cefradine, cefroxadine, ceftezole, cefaloglycin, cefacetrile, cefalonium, cfaloridine, cefalotin, cefatrizine, cefaclor, cefotetan, cephamycin, cefoxitin, cefprozil, cefuroxime, cefuroxime axetil, cefamandole, cefminox, cefonicid, ceforanide, cefotiam, cefbuperazone, cefuzonam, cefmetazole, carbacephem, loracarbef, cefixime, ceftriaxone, antipseudomonal, ceftazidime, cefoperazone, cefdinir, cefcapene, cefdaloxime, ceftizoxime, cefmenoxime, cefotaxime, cefpiramide, cefpodoxime, ceftibuten, cefditoren, cefetamet, cefodizime, cefpimizole, cefsulodin, cefteram, ceftiolene, oxacephem, flomoxef, latamoxef, cefepime, cefozopran, cefpirome, cefquinome, ceftaroline fosamil, ceftolozane, ceftobiprole, ceftiofur, cefquinome, cefovecin, aztreonam, tigemonam, carumonam, and nocardicin A.

Non-limiting examples of fluoroquinolone include enoxacin, ciprofloxacin, norfloxacin, ofloxacin, levofloxacin, trovafloxacin, gatifloxacin, or moxifloxacin.

A person of ordinary skill in the art can envision that any drug that can be acrylolated to produce the homopolymers according to this disclosure and such embodiments are within the purview of the invention.

In preferred embodiments, a homopolymer of an acrylolated drug is in the form of nanoparticles. In preferred embodiments, the nanoparticle have a size of between 600 nm and 1000 nm, preferably, between 700 nm and 1000 nm, even more preferably, between 800 nm and 1000 nm, and most preferably, between 900 nm and 1000 nm. In a particular embodiment, the nanoparticles have a size of about 970 nm.

In other embodiments, the nanoparticles further comprise a detergent. In more preferred embodiments, the nanoparticles containing a detergent are in the form of an aqueous emulsion. Non-limiting examples of detergents that can be included in the nanoparticles or the emulsions disclosed herein include sodium dodecyl sulfate, cetyltrimethylammonium bromide, 3-(N,N-dimethylmyristylammonio)propanosulfonate, dedecanoic acid 2-(2-hydroxyethoxy)ethyl ester, sodium 11-(acrylolyloxyundecan-1-yl) sulfate, N-(11-Acryloyloxyundecyl)-N-(2-hydroxyethyl)-N,N-dimethylammoniuim bromide, N-(11-Acryloyloxyundecyl)-N,N-dimethyl-N-ethylammonium bromide, 3-[N,N-Diethyl-N-(3-sulfopropyl)ammonio] acrylate, 2(2-Acryloyloxyethoxy) ethyl dodecanoate, or any mixture thereof.

Certain other embodiments of the invention provide a co-polymer of two or more acrylolated drugs. Such co-polymers can be useful for administering a combination of drugs in one composition. A person of ordinary skill in the art can select appropriate combination of two or more drugs that can be acrylolated and formed into a co-polymer. Much like the homopolymers described herein, such co-polymers can also be in the form of nanoparticles comprising the co-polymers of acrylolated drugs, or emulsions containing the nanoparticles of the co-polymers of acrylolated drugs of the invention. Further, the methods described herein for producing homopolymers of acrylolated drugs can be readily modified to produce the co-polymers of two or more acrylolated drugs by simply mixing appropriate amounts of monomers of the corresponding acrylolated drugs.

Specific embodiments of the invention provide a method of producing an aqueous emulsion of a homopolymer of an acrylate monomer of a drug. Such method comprises the steps of:

a) dissolving the acrylolated monomer of the drug in an organic solvent;

b) dissolving a detergent in water;

c) mixing the solution of detergent in water with the solution of the acrylolated monomer of the drug in the organic solvent;

d) increasing the temperature of the mixture produced in step c);

e) contacting the mixture produced in step d) to an oxidant that initiates polymerization of the acrylate monomers of the drug; and optionally, additional water;

f) stirring the mixture produced in step e) to produce the aqueous emulsion of the homopolymer of the acrylate monomer of the drug.

In certain embodiments, the step of dissolving a detergent in water is performed at a temperature between 25° C. and 45° C., preferably, at a temperature between 30° C. and 40° C., more preferably, at a temperature of about 35° C.

In preferred embodiments, the step of increasing the temperature of the mixture produced in step c) is performed under constant stirring. The temperature of the mixture produced in step c) can be increased to between 80° C. and 110° C., preferably, between 85° C. and 105° C., even more preferably, between 90° C. and 100° C., and most preferably, to about 95° C.

A person of ordinary skill in the art can select a suitable organic solvent to dissolve an acrylolated drug. Organic solvents that can be used include methanol, ethanol, propylene glycol, hexane, glycerol, ethyl acetate, dichloromethane, or any mixture thereof. An organic solvent is selected that would evaporate at a temperature of between 80° C. and 110° C. and thus, can be removed from the mixture during the process of making the aqueous emulsion. Additional examples of organic solvents that can be used in the methods of the invention are well known to a person of ordinary skill in the art and such embodiments are within the purview of the invention.

A detergent suitable for use in the methods of the invention include sodium dodecyl sulfate, cetyltrimethylammonium bromide, 3-(N,N-dimethylmyristylammonio)propanosulfonate, dedecanoic acid 2-(2-hydroxyethoxy)ethyl ester, sodium 11-(acrylolyloxyundecan-1-yl) sulfate, N-(11-Acryloyloxyundecyl)-N-(2-hydroxyethyl)-N,N-dimethylammoniuim bromide, N-(11-Acryloyloxyundecyl)-N,N-dimethyl-N-ethylammonium bromide, 3-[N,N-Diethyl-N-(3-sulfopropyl)ammonio]acrylate, 2(2-Acryloyloxyethoxy) ethyl dodecanoate, or any mixture thereof. Additional examples of detergents that can be used in the methods of the invention are well known to a person of ordinary skill in the art and such embodiments are within the purview of the invention.

In preferred embodiments, dissolving an acrylate monomer of a drug in an organic solvent is performed at a temperature of between 35° C. and 45° C., i.e., at a temperature higher than the room temperature. Such temperature facilitates dissolution of the drug in the organic solvent.

The step of increasing the temperature of the mixture produced in step c) to between 80° C. and 100° C. is performed at a rate of between 5° C. and 15° C. per hour, preferably, at a rate of between 6° C. and 14° C. per hour, more preferably, at a rate of between 7° C. and 13° C. per hour, even more preferably, at a rate of between 8° C. and 12° C. per hour, and most preferably, at a rate of between 9° 12° C. and 11° C. per hour, and particularly, at a rate of about 10° C. per hour. Such slow increase in temperature ensures proper formation of homopolymers while slowly evaporating the organic solvent out of the mixture, thus producing an aqueous suspension of the homopolymeric nanoparticles.

Evaporation of the organic solvent from the mixture produced in step d) can be further facilitated by constant stirring, for example, at a rate of between 800 rpm to 1300 rpm, preferably, at a rate of between 900 rpm to 1200 rpm, more preferably, at a rate of between 1000 to 1100 rpm, and even more preferably, at a rate of 1100 rpm.

Preferably, the oxidant that initiates polymerization is a radical initiator. Examples of oxidant that initiates polymerization of the acrylate monomers include potassium persulfate.

In preferred embodiments, the step of polymerization and stirring (steps e) and f) above) are carried out for between 36 to 60 hours, preferably, between 40 to 56 hours, more preferably, between 44 to 52 hours, and most preferably, for about 48 hours.

In certain embodiments, the drug used in the methods of the invention is an antibiotic. Examples of antibiotics mentioned above in connection with the homopolymers of the invention can also be used in the methods of the invention. Also, additional drugs or antibiotics that can be used in the methods of the invention can be readily identified by a person of ordinary skill in the art and such embodiments are within the purview of the invention. Further, for co-polymers containing a combination of drugs or a combination of antibiotics, a person of ordinary skill in the art can select appropriate combinations of drugs based on intended applications.

The homopolymers, nanoparticles containing such homopolymers, and emulsions containing the nanoparticles disclosed herein exhibit the activity of the drug, for example, the antibiotic used to produce the homopolymer. Accordingly, certain embodiments of the invention provide a method of treating a disease in a subject by administering a therapeutically effective amount of a homopolymers, nanoparticles containing such homopolymers, or emulsions containing the nanoparticles disclosed herein.

Co-polymers of a combination of acrylolated drugs, nanoparticles containing such co-polymers, and emulsions containing the nanoparticles of such co-polymers can also be in the methods of treating a disease disclosed herein.

In preferred embodiments, the disease is an infection caused by an infectious agent and the homopolymer is produced from an acrylolated antibiotic. Accordingly, certain embodiments of the invention provide methods of treating an infection in a subject caused by an infectious agent, the method comprising administering to the subject the homopolymers, nanoparticles containing such homopolymers, or emulsions containing the nanoparticles disclosed herein. The homopolymers, nanoparticles, or emulsions disclosed herein can be administered in the form of a pharmaceutical composition comprising pharmaceutically acceptable carriers.

The polymers (including homopolymers and co-polymers disclosed herein), nanoparticles, or emulsions can be administered via, for example, oral, pulmonary, buccal, suppository, intravenous, intraperitoneal, intranasal, intramuscular or subcutaneous routes. Additional routes of administration are well known to a skilled artisan and such embodiments are within the purview of this invention. The appropriate route of administration depends on the type of disease being treated, the subject being treated, the stage and severity of the disease, etc. A person of ordinary skill in the art can determine an appropriate route of administration based on specific parameters.

In certain embodiments, the disease is an infection caused by a virus, bacterium, protozoan, helminth, archaebacterial, or a fungus. A person of ordinary skill in the art can select an appropriate drug or combination of drugs to treat an infection and produce the corresponding polymers, nanoparticles, or emulsions based on this disclosure.

Routes of Administration and Dosage Forms

In certain embodiments, the polymers, nanoparticles, or emulsions can be administered intramuscularly, subcutaneously, intrathecally, intravenously or intraperitoneally by infusion or injection. Solutions of the polymers, nanoparticles, or emulsions can be prepared in water, optionally mixed with a nontoxic surfactant. Under ordinary conditions of storage and use, these preparations can contain a preservative to prevent the growth of microorganisms.

The pharmaceutical dosage forms suitable for injection or infusion can include sterile aqueous solutions or dispersions comprising the polymers, nanoparticles, or emulsions, that are adapted for the extemporaneous preparation of sterile injectable or infusible solutions or dispersions. Preferably, the ultimate dosage form should be sterile, fluid, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained by, for example, the formation of liposomes, by the maintenance of the required particle size in the case of dispersions, or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by the use in the compositions of agents delaying absorption, for example, aluminum monostearate and gelatin.

Sterile injectable solutions are prepared by incorporating the polymers, nanoparticles, or emulsions in the required amount in the appropriate solvent as described herein with various of the other ingredients enumerated herein, as required, preferably followed by filter sterilization. In the case of sterile powders for the preparation of sterile injectable solutions, the preferred methods of preparation are vacuum drying and freeze drying techniques, which yield a powder the polymers, nanoparticles, or emulsions plus any additional desired ingredient present in the previously sterile-filtered solutions.

The compositions of the subject invention may also be administered orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the subject's diet.

For oral therapeutic administration the polymers, nanoparticles, or emulsions can be combined with one or more excipients and used in the form of ingestible tablets, buccal tablets, troches, capsules, elixirs, suspensions, syrups, wafers, and the like. The percentage of the polymers, nanoparticles, or emulsions present in such compositions and preparations can be varied can be conveniently be between about 2% to about 60% of the weight of a given unit dosage form. The amount of the polymers, nanoparticles, or emulsions in such therapeutically useful compositions is such that an effective dosage level will be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid, and the like; a lubricant such as magnesium stearate; and a sweetening agent such as sucrose, fructose, lactose, or aspartame, or a flavoring agent such as peppermint, oil of wintergreen, or cherry flavoring may be added.

When the unit dosage form is a capsule, it may contain, in addition to materials of the above type, a liquid carrier, such as a vegetable oil or a polyethylene glycol.

Various other materials may be present as coatings or for otherwise modifying the physical form of the solid unit dosage form. For instance, tablets, pills, or capsules may be coated with gelatin, wax, shellac, or sugar, and the like. A syrup or elixir can contain the polymers, nanoparticles, or emulsions and sucrose or fructose as a sweetening agent, methyl and propylparabens as preservatives, a dye, and flavoring such as cherry or orange flavor.

Any material used in preparing any unit dosage form should be pharmaceutically acceptable and substantially non-toxic in the amounts employed.

In addition the polymers, nanoparticles, or emulsions can be incorporated into sustained-release preparations and devices. For example, the polymers, nanoparticles, or emulsions can be incorporated into time release capsules, time release tablets, time release pills, and time release polymers or nanoparticles.

Pharmaceutical compositions for topical administration of the polymers, nanoparticles, or emulsions to the epidermis (mucosal or cutaneous surfaces) can be formulated as ointments, creams, lotions, gels, or as a transdermal patch. Such transdermal patches can contain penetration enhancers such as linalool, carvacrol, thymol, citral, menthol, t-anethole, and the like. Ointments and creams can, for example, include an aqueous or oily base with the addition of suitable thickening agents, gelling agents, colorants, and the like. Lotions and creams can include an aqueous or oily base and typically also contain one or more emulsifying agents, stabilizing agents, dispersing agents, suspending agents, thickening agents, coloring agents, and the like. Gels preferably include an aqueous carrier base and include a gelling agent such as cross-linked polyacrylic acid polymer, a derivatized polysaccharide (e.g., carboxymethyl cellulose), and the like.

Pharmaceutical compositions suitable for topical administration in the mouth (e.g., buccal or sublingual administration) include lozenges comprising the composition in a flavored base, such as sucrose, acacia, or tragacanth; pastilles comprising the composition in an inert base such as gelatin and glycerin or sucrose and acacia; and mouthwashes comprising the active ingredient in a suitable liquid carrier. The pharmaceutical compositions for topical administration in the mouth can include penetration enhancing agents, if desired.

Useful solid carriers include finely divided solids such as talc, clay, microcrystalline cellulose, silica, alumina, and the like. Other solid carriers include nontoxic polymeric nanoparticles or microparticles. Useful liquid carriers include water, alcohols, or glycols, or water/alcohol/glycol blends, in which the polymers, nanoparticles, or emulsions can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of useful dermatological compositions that can be used to deliver the polymers, nanoparticles, or emulsions to the skin are known in the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508), all of which are hereby incorporated by reference.

The concentration of the polymers, nanoparticles, or emulsions in such formulations can vary widely depending on the nature of the formulation and intended route of administration. For example, the concentration of the homopolymers, nanoparticles, or emulsions in a liquid composition, such as a lotion, can preferably be from about 0.1-25% by weight, or, more preferably, from about 0.5-10% by weight. The concentration in a semi-solid or solid composition such as a gel or a powder can preferably be about 0.1-5% by weight, or, more preferably, about 0.5-2.5% by weight.

Pharmaceutical compositions for spinal administration or injection into amniotic fluid can be provided in unit dose form in ampoules, pre-filled syringes, small volume infusion, or in multi-dose containers, and can include an added preservative. The compositions for parenteral administration can be suspensions, solutions, or emulsions, and can contain excipients such as suspending agents, stabilizing agents, and dispersing agents.

A pharmaceutical composition suitable for rectal administration comprises the polymers, nanoparticles, or emulsions in combination with a solid or semisolid (e.g., cream or paste) carrier or vehicle. For example, such rectal compositions can be provided as unit dose suppositories. Suitable carriers or vehicles include cocoa butter and other materials commonly used in the art.

According to one embodiment, pharmaceutical compositions of the present invention suitable for vaginal administration are provided as pessaries, tampons, creams, gels, pastes, foams, or sprays containing the polymers, nanoparticles, or emulsions in further combination with carriers known in the art. Alternatively, compositions suitable for vaginal administration can be delivered in a liquid or solid dosage form.

Pharmaceutical compositions suitable for intra-nasal administration are also encompassed by the present invention. Such intra-nasal compositions comprise the polymers, nanoparticles, or emulsions in a vehicle and suitable administration device to deliver a liquid spray, dispersible powder, or drops. Drops may be formulated with an aqueous or non-aqueous base also comprising one or more dispersing agents, solubilizing agents, or suspending agents. Liquid sprays are conveniently delivered from a pressurized pack, an insufflator, a nebulizer, or other convenient means of delivering an aerosol comprising the polymers, nanoparticles, or emulsions. Pressurized packs comprise a suitable propellant such as dichlorodifluoromethane, trichlorofluoromethane, dichlorotetrafluoroethane, carbon dioxide, or other suitable gas as is well known in the art. Aerosol dosages can be controlled by providing a valve to deliver a metered amount of the homopolymers, nanoparticles, or emulsions.

The polymers, nanoparticles, or emulsions can be combined with an inert powdered carrier and inhaled by the subject or insufflated.

Pharmaceutical compositions for administration by inhalation or insufflation can be provided in the form of a dry powder composition, for example, a powder mix of the homopolymers, nanoparticles, or emulsions and a suitable powder base such as lactose or starch. Such powder composition can be provided in unit dosage form, for example, in capsules, cartridges, gelatin packs, or blister packs, from which the powder can be administered with the aid of an inhalator or insufflator.

The exact amount (effective dose) of the polymers, nanoparticles, or emulsions administered can vary from subject to subject, depending on, for example, the species, age, weight, and general or clinical condition of the subject, the severity or mechanism of any disorder being treated, the particular agent or vehicle used, the method and scheduling of administration, and the like. A therapeutically effective dose can be determined empirically, by conventional procedures known to those of skill in the art. See, e.g., The Pharmacological Basis of Therapeutics, Goodman and Gilman, eds., Macmillan Publishing Co., New York. For example, an effective dose can be estimated initially either in cell culture assays or in suitable animal models. The animal model may also be used to determine the appropriate concentration ranges and routes of administration. Such information can then be used to determine useful doses and routes for administration in humans. Methods for the extrapolation of effective dosages in mice and other animals to humans are known to the art; for example, see U.S. Pat. No. 4,938,949, which is hereby incorporated by reference. A therapeutic dose can also be selected by analogy to dosages for comparable therapeutic agents.

The particular mode of administration and the dosage regimen will be selected by the attending clinician, taking into account the particulars of the case (e.g., the subject, the disease, the disease state involved, and whether the treatment is prophylactic). Treatment may involve daily or multi-daily doses of compound(s) over a period of a few days to months, or even years.

In general, however, a suitable dose will be in the range of from about 0.001 to about 100 mg/kg of body weight per day, preferably from about 0.01 to about 100 mg/kg of body weight per day, more preferably, from about 0.1 to about 50 mg/kg of body weight per day, or even more preferred, in a range of from about 1 to about 10 mg/kg of body weight per day. For example, a suitable dose may be about 1 mg/kg, 10 mg/kg, or 50 mg/kg of body weight per day.

The polymers, nanoparticles, or emulsions can be conveniently administered in unit dosage form, containing for example, about 0.05 to about 10000 mg, about 0.5 to about 10000 mg, about 5 to about 1000 mg, or about 50 to about 500 mg of the homopolymers, nanoparticles, or emulsions.

The polymers, nanoparticles, or emulsions can be administered to achieve peak plasma concentrations of, for example, from about 0.25 to about 200 µM, about 0.5 to about 75 µM, about 1 to about 50 µM, about 2 to about 30 µM, or about 5 to about 25 µM of each of the drug. Exemplary desirable plasma concentrations include at least 0.25, 0.5, 1, 5, 10, 25, 50, 75, 100 or 200 µM. For example, plasma levels may be from about 1 to about 100 micromolar or from about 10 to about 25 micromolar. This may be achieved, for example, by the intravenous injection of a 0.05 to 5% solution of the polymers, nanoparticles, or emulsions in saline, or orally administered as a bolus containing about 1 to about 100 mg of the homopolymers, nanoparticles, or emulsions. Desirable blood levels may be maintained by continuous or intermittent infusion.

The polymers, nanoparticles, or emulsions can be included in the compositions within a therapeutically useful and effective concentration range, as determined by routine methods that are well known in the medical and pharmaceutical arts. For example, a typical composition can include the polymers, nanoparticles, or emulsions at a concentration in the range of at least about 1 mg/ml, preferably at least about 4 mg/ml, more preferably at least 5 mg/ml and most preferably at least 6 mg/ml.

The polymers, nanoparticles, or emulsions can conveniently be presented in a single dose or as divided doses administered at appropriate intervals, for example, as one dose per day or as two, three, four or more sub-doses per day. The sub-dose itself may be further divided, e.g., into a number of discrete loosely spaced administrations; such as multiple inhalations from an insufflator.

Optionally, the pharmaceutical compositions of the present invention can include one or more other therapeutic agents, e.g., as a combination therapy. The additional therapeutic agent(s) will be included in the compositions within a therapeutically useful and effective concentration range, as determined by routine methods that are well known in the medical and pharmaceutical arts. The concentration of any particular additional therapeutic agent may be in the same range as is typical for use of that agent as a monotherapy, or the concentration may be lower than a typical monotherapy concentration if there is a synergy when combined with the homopolymers, nanoparticles, or emulsions.

Following example illustrates procedures for practicing the invention. This example should not be construed as limiting.

Example 1 Polyacrylate Nanoparticle Emulsions: Forming Homo Poly (N-Acryloylciprofloxacin) as an Antibacterial Polymer Emulsion The possibility of removing all non-bioactive monomers from nanoparticle construction was explored. Avoiding the use of co-monomers during the emulsion polymerization procedure allows for greater amount of loading of the bioactive antibacterial monomer, producing a homopolymer nanoparticle emulsion composed solely of the antibiotic monomer.

This Example delves into tackling the issue of limited loading of bioactive compounds, and the need for a better carrier polymer to bind or encapsulate the drug for delivery. The surfactant has a limit of how many organic/hydrophobic compounds it can contain within the micelle during emulsion polymerization. As a result, the maximum amount of organic content of the final emulsion is typically in the range of 15-20% by weight. This restricts the usefulness of the nanoparticle as an effective drug carrier to 20% or less of the emulsion amount.

Polyacrylate nanoparticle emulsions can be easily prepared through radical-induced emulsion polymerization of butyl acrylate/styrene mixtures (7:3 w/w) in water at 78° C., using sodium dodecyl sulfate (SDS) as an emulsifying agent and potassium persulfate as a radical initiator (FIG. 1). The reactions led to the formation of a homogeneous, stable aqueous emulsion containing uniformly-sized nanoparticles of 45-50 nm in diameter. The method was successfully applied to penicillins and N-thiolated β-lactams, in which the antibacterial agents could be introduced into the nanoparticle either by non-covalent entrapment as a free drug, or covalently via their acryloyl derivative.

While these earlier nanoparticle emulsions provided increased water solubility and, in some cases, improved bioactivity of the β-lactam antibacterial agent, the polyacrylate backbone was largely comprised of the non-bioactive monomers (butyl acrylate-styrene or methyl methacrylate-styrene (20% by weight of the emulsion), and thus only 1-3% (by weight) of the nanoparticle framework was the antibacterial acrylate. FIG. 1 shows the general scheme for the formation of the nanoparticle emulsion, and the amount of drug loading into the nanoparticle during the assembly process was limited by how much surfactant could be used, given that amounts exceeding 3 mole % of SDS caused unwanted cytotoxicity. The final crude nanoparticle emulsions contained up to 20% of solid content (a mixture of nanoparticles and a small amount of non-nanoparticle polymer), and only 0.2-0.6% of active antibacterial agent inside of the nanoparticles. The resulting emulsions are typically milky in consistency and somewhat sticky when exposed to air, causing films to form when dried, and forming coagulants within syringes, micro-porous filters, and gel columns that made it very difficult to purify and use for in vivo testing.

Purification techniques that enable the removal of residual unreacted monomers and non-nanoparticle oligomers within the cloudy emulsion were used. Other surfactant combinations were used to try to enhance the amount of antibiotic that could be entrapped, or to alter nanoparticle sizes, without increasing overall cytotoxicity or instability of the emulsion.

FIG. 2 depicts the polyacrylate polymer that was formed that allows for the incorporation of the bioactive drug either through covalently binding to the polymer backbone or encapsulating within the hydrophobic environment of the micelle. This in turn limits the amount of bioactive drug that can be contained in the particle.

FIG. 3 shows that removing all acrylates except for the acrylolated bioactive drug (or other compound) for the emulsion polymerization would allow for an increase in the ability to load the desired drugs/compounds within the micelles, and thus the final concentration in the nanoparticle emulsion. If the same limit of 15-20% of organic material entrapped by the surfactant inside the micelles is maintained, then the final concentration of the drug incorporated into the nanoparticle would be considerably more than the typical 0.2%-0.6% achieved using the butyl acrylate/styrene polyacrylate nanoparticles. The use of only N-acryloylciprofloxacin as the sole monomer then would afford an advanced polyacrylate nanoparticle emulsion, which allows for the delivery of higher drug content. This would in return require much smaller volumes of the emulsion to be synthesized and used for drug delivery.

The avoidance of using other monomers for the nanoparticle formation additionally removes the issue of unwanted coagulation and film formation previously observed for the poly(butyl acrylate/styrene) nanoparticle emulsions. The residual styrene and butyl acrylate and non-particle polymers that are not encapsulated within the surfactant could be removed by centrifugation and dialysis, however, the resulting emulsions after purification still continued to formed rubbery films when dehydrated, which clogged syringe needles and filtration membranes. The use of these particular monomers was problematic in this regard and not using them might eliminate the need to purify the ciprofloxacin acrylate emulsions.

In this Example, a new approach to preparing antibiotic-bound polyacrylate nanoparticle emulsions is described that completely obviates the restriction of using butyl acrylate and styrene (or other co-monomers) to form the nanoparticle framework, and instead, uses the antibiotic compound itself as the sole acrylate monomer for the polymerization. This technique has never been reported and is thus an important advance in the polymer-based nanoparticle field.

Ciprofloxacin was chosen as the antibiotic for the formation of the polyacrylate nanoparticles. The N-acryloyl derivative of commercial ciprofloxacin hydrochloride was prepared for this purpose according to N-acylation procedure.

Synthesis of N-Acryloylciprofloxacin

FIG. 4 shows the synthetic scheme for preparing N-acryloyl ciprofloxacin, and follows as such: To a round bottom flask was added 120 ml of dichloromethane, then 3.0 g (9.0 mmol) of ciprofloxacin and 1.8 ml (13.5 mmol) of triethylamine. The mixture was left stirring at 0° C. for 1 hour then acryloyl chloride (1.1 ml, 13 mmol) was added dropwise. The ice bath was removed and the reaction was left stirring overnight. The dichloromethane was added dropwise to a flask of hexane (200 ml) to cause a precipitate to form. The solid was collected by filtration and allowed to air dry.

Yielded 2.90 g (83.7%) as a pale yellow solid. Melting point above 250° C. $^1$H NMR (400 MHz, $CDCl_3$) δ 8.75 (s, 1H), 8.03 (d, J=12.8 Hz, 1H), 7.36 (d, J=7.1 Hz, 1H), 6.60 (dd, J=16.8, 10.5 Hz, 1H), 6.35 (dd, J=16.8, 1.7 Hz, 1H), 5.76 (dd, J=10.5, 1.7 Hz, 1H), 3.86 (m, 4H), 3.52 (br. s., 1H), 3.33 (m, 4H), 1.38 (d, J=6.2 Hz, 2H), 1.19 (br. s., 2H).

Formation of Poly(N-Acryloylciprofloxacin) Nanoparticle Emulsion

One of the main challenges with polymerizing the desired acryloyl analog of the bioactive drug was that most of the previous antibiotics that were acrylolated and loaded into the nanoparticle emulsions were solids, and thus the liquid organic monomers of styrene and butyl acrylate could be used to pre-dissolve the small amount of the solid acrylolated antibiotic. This was also the case with the poly (menthyl acrylate) nanoparticle emulsions, in that the non-bioactive monomer menthyl acrylate was a liquid that allowed for the dissolution of the solid N-acryloyl ciprofloxacin antibiotic in order to be incorporated into micelles during emulsion polymerization.

Attempts to use the same procedure for emulsion polymerization of the N-acrylolated ciprofloxacin monomer failed, however. Thus it was necessary to pre-dissolve the N-acryloyl ciprofloxacin into an organic solvent that could easily be evaporated off during the polymerization process or after the formation of the emulsions.

It was considered important to use a solvent of very low cytotoxicity to aid in the dissolution of the bioactive compounds, in case it would also load into the micelles along with the bioactive compound. After experimentation with various common organic solvents, including methanol, ethanol, propylene glycol, glycerol, and ethyl acetate; dichloromethane was chosen.

Attempted Preparation of Homo Poly(N—N-Acryloylciprofloxacin) Nanoparticle Emulsions Using Water-Soluble Organic Solvents Two liquid organic solvents were first used to aid the dissolution of N-acryloylciprofloxacin. Propylene glycol and glycerin have very low cytotoxicity and due to their hydrophobic nature would likely load into the surfactant-formed micelles, and thus potentially carry in with it the N-acryloylciprofloxacin. Though this technique would result in a co-solvent also being incorporated into the micelles, it would still possibly allow for formation of the poly(N-acryloylciprofloxacin) emulsion.

However, the resulting emulsions formed from the use of these solvents were not homogeneous. Due to glycerin's high viscosity, it was very difficult to distribute and stir properly in the aqueous media. This led to a bilayer, preventing homogeneous mixing of the resulting emulsion. The mixture was heated up to 90° C. in order to reduce the viscosity and allow for more uniform stirring and mixing with water. However, the resulting emulsions remained non-homogeneous.

Propylene glycol provided a much better carrier solvent due to its lower viscosity. It was able to form a more uniform emulsion and would require no modification in procedure compared to the typical one used to make polyacrylate nanoparticle emulsions. However, the resulting emulsions were unstable and formed a bilayer within minutes of being removed from the polymerization conditions. The DLS data did confirm multiple populations of particles within the emulsion and very low zeta potential values (−5 mV to −10 mV), which confirmed the inherent instability of the emulsions. So these attempts did not prove effective.

Preparation of Homo Poly(N-Acryloylciprofloxacin) Nanoparticle Emulsions Using a Water-insoluble Solvent.

The other method investigated for polymerization of the solid N-acryloylciprofloxacin to be evenly distributed within the aqueous mixture was to pre-dissolve the compound in an organic solvent, and then remove the organic solvent via evaporation during the emulsion process or after the emulsion formation. It was critical to completely remove the organic solvent, because most organic solvents produce cytotoxicity.

This method was attempted using methanol, ethanol, ethyl acetate, and dichloromethane. The main problem was the poor solubility of the N-acryloylciprofloxacin in most organic solvents, except for dichloromethane. Up to 500 mg/ml of N-acryloylciprofloxacin could be dissolved into dichloromethane. However, there was a critical issue that resulted with the polymerization procedure. Typically, organics were stirred at 75° C., then the surfactant and water were added. This would cause the dichloromethane to rapidly evaporate. Thus the starting temperature was adjusted to 25° C., and water and surfactant were added to the stirring dichloromethane solution, however this resulted in an uneven distribution and clumping of the surfactant. The result was a very sticky material that separated from the water layer.

To solve this, the surfactant and water were added first at 75° C. so that the surfactant may form micelles initially, and the dichloromethane solution was added dropwise. However, this resulted in the near instant evaporation of the dichloromethane solvent, leaving clumps of solid N-acryloylciprofloxacin unincorporated into the micelles. The final adjustment of the procedure is discussed in the following section, resulting in successful formation of the emulsion.

Preparation of Poly(N-Acryloylciprofloxacin) Nanoparticle Emulsions

Figure 5:
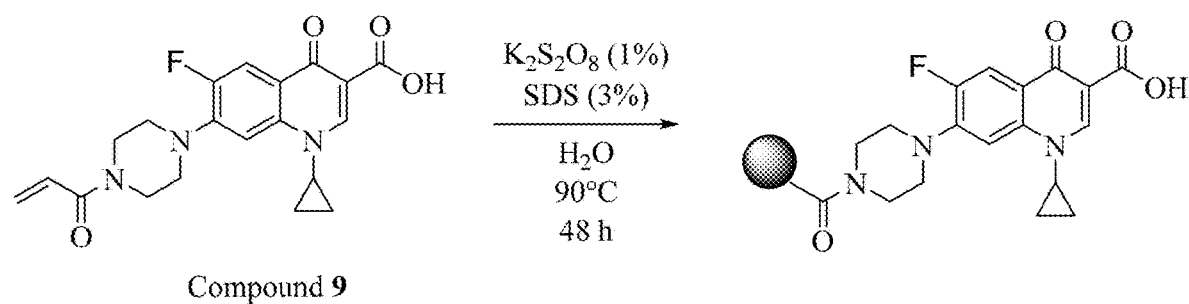
FIG. 5. Scheme for poly(N-acryloylciprofloxacin) nanoparticle emulsions.

As seen in FIG. 5, the polyacrylate emulsions were prepared using a modified protocol of the usual nanoparticle emulsion technique used in our lab. The method to form the poly(N-acryloylciprofloxacin) emulsion required the following procedure: to a round bottom flask was added 4 ml of deionized water, which was then stirred using a 1.25 cm (300 mg) Teflon-coated magnetic stir bar at 1000 rpm on a Corning PC-420D magnetic stirrer at 30° C. using a self-regulated oil bath. To this was added 30 mg of SDS. N-Acryloylciprofloxacin (500 mg) was dissolved in 1 ml of warm dichloromethane, and this solution was added dropwise to the deionized water-SDS mixture. A vent was placed on top of the flask by inserting a small stainless steel syringe needle through a rubber septum on the flask, under dry nitrogen, and the temperature of the mixture was increased at a rate of 5° C. per 30 min until reaching 90° C. The mixture was left stirring overnight at this temperature, under an atmosphere of dry nitrogen. Potassium persulfate (10 mg) was added with an additional 0.5 ml of deionized water to the stirring mixture, and left stirring for 24 hours. The stirred emulsion was then removed from the oil bath and decanted into a storage vial for analysis.

Figure 6:
FIG. 6. On the left, an example of a successful emulsion. On the right, two examples of unsuccessful emulsions.

FIG. 6 shows an example of a successful emulsion (on the left), forming a uniform single layer emulsion, while previous attempted emulsions (the two on the right) show the results of an unsuccessful emulsion polymerization.

Dynamic Light Scattering (DLS) Analysis

Dynamic light scattering measurements were performed to test if any nanoparticles were being formed in the emulsion polymerization process. The average size and surface charge of the emulsion was analyzed on a Malvern Zetasizer nano-ZS instrument. To prepare the samples for the analyses, the freshly-made emulsion was subjected to centrifugation at 10,000 rpm for 5 min using an Eppendorf Centrifuge 5424. An aliquot of the liquid emulsion was then drawn and deposited into a Malvern disposable folded capillary cell DTS-1070. Each sample was analyzed in triplicate, and each data collection consisted of 1 run of 20 scans (for size analysis) and 3 runs of 100 scans (for zeta potential determination). The size distribution shows a single narrow peak indicating the uniformity of the emulsion with a single population centered on average at approximately 970 nm. Similarly, surface charge measurements indicated a highly stable emulsion, with an average of −63 (±5.6) mV.

Dynamic Light Scattering (DLS) Analysis Results

Figure 7:
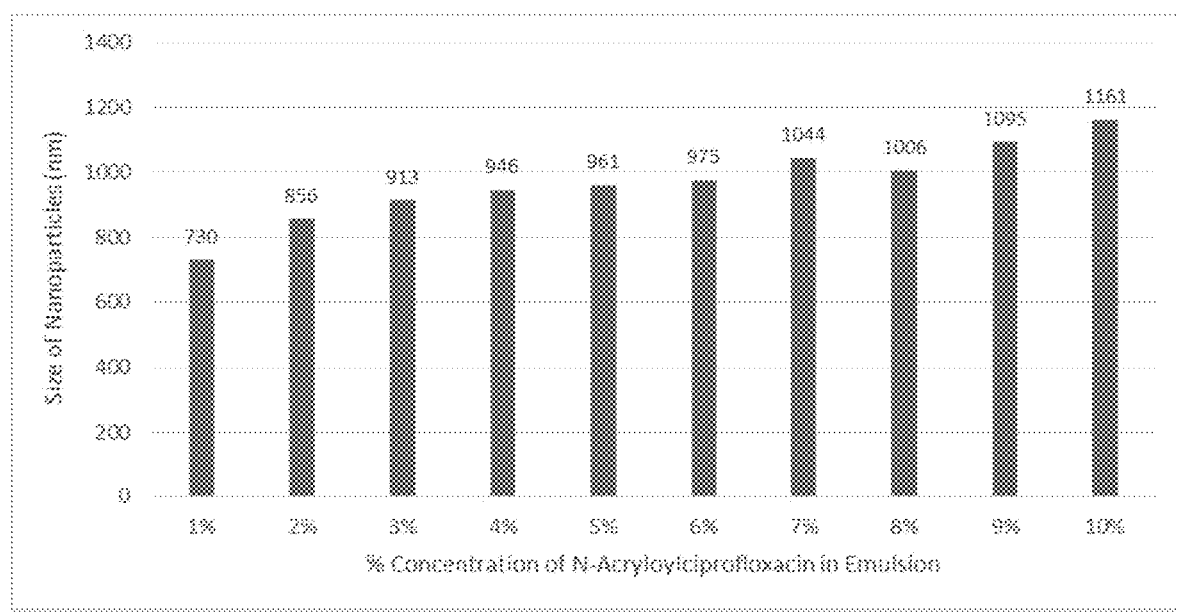
FIG. 7. Size of emulsified nanoparticles vs the % concentration of N-acryloyl ciprofloxacin in the emulsions.

As FIG. 7 demonstrates, the dynamic light scattering experiments confirmed the presence of a major population of nanoparticles in the emulsion, measuring on average approximately 970 nm in diameter. A general trend of increasing size was observed as the amount of N-acryloylciprofloxacin is increased in forming the polymer emulsions. In addition, the zeta potential measurements showed that the particles carry a high surface charge of −63 (±5.6) mV. This indicates the long-term stability of the emulsion. It is notable that these poly(N-acryloylciprofloxacin) nanoparticles are much larger than those previously constructed with butyl acrylate-styrene co-monomers, which routinely measured 45-50 nm in diameter. The basis for this 20-fold increase in size is not apparent at this time but deserves further investigation.

In Vitro Antibacterial Testing

To investigate whether the nanoparticles possess antibiotic capabilities, each crude emulsion was tested against *Staphylococcus aureus* (ATCC 25923) and *Escherichia coli* (K12) using a 96-well plate broth assay to determine the minimum inhibitory concentration (MIC). Each assay was done in triplicate.

The original stock emulsion was diluted using the Trypticase Soy Broth solution to an initial concentration of 1.28 mg/ml of the N-acryloylciprofloxacin, then serial diluted with TSB to half the concentration each time. A volume of 10 µl of each emulsion dilution was added to a well in series, resulting in a final concentration run of 64 µg/ml to 0.012 µg/ml. The MIC was done in triplicates for each bacterium, with ciprofloxacin hydrochloride being used as a positive control and a blank of broth medium was used as a negative control.

Bacteria were grown overnight at 37° C. on an agar plate composed of BBL TSA II Trypticase Soy Agar (TSA) and BBL Trypticase Soy Broth (TSB) in a 1:2 ratio at 4.4% concentration. A broth solution of 2.4% TSB was inoculated using the bacteria from the agar plates, and incubated at 37° C. to reach a 0.5 McFarland standard. The bacteria were then further diluted by a factor of 1000 using a broth solution of 2.4% TSB, and 190 µl of the diluted bacterial solution was transferred by micropipette into each well. The inoculated plates were incubated at 37° C. for 16-20 hours and the resulting plates were observed for growth and MIC values recorded. The MIC was the lowest concentration of the antibiotic that completely inhibited bacterial growth (visually) within that series of dilutions.

Antibacterial Data for Poly (N-Acryloylciprofloxacin) Emulsions

TABLE 1

MIC values of ciprofloxacin and ciprofloxacin emulsion vs *S. aureus* and *E. coli*.

| Sample | *S. aureus* (ATCC 25923) | *E. coli* (K12) |
|---|---|---|
| Control Ciprofloxacin | 0.5 µg/ml | 0.012 µg/ml |
| Poly (N-acryloyl-ciprofloxacin) emulsion | 0.5 µg/ml | 0.012 µg/ml |

The in vitro antibacterial studies showed that the nanoparticle emulsion was bioactive, with an MIC of 0.5 µg/ml for *S. aureus* and 0.012 µg/ml against *E. coli*, identical to those of ciprofloxacin itself (Table 1). The finding that these nanoparticles show antibacterial capabilities against both the gram-positive *S. aureus* and the gram-negative *E. coli* was surprising, given that particles of such large dimensions would not be expected to be antibacterially active.

Ciprofloxacin must enter the bacterial cell to arrive at its target, bacterial DNA gyrase. Attachment of the molecule to the polymer backbone of the nanoparticle requires it be released through hydrolysis of the amide. This occurs either outside of the cell or within the bacterium itself if the nanoparticle can enter through the membrane. Most likely this requires enzymatic release, as the amide functionality is a difficult one to cleave otherwise.

In Vitro Cytotoxicity of the Nanoparticle Emulsions

In vitro cell cytotoxicity was tested on two human cell lines, human colorectal carcinoma cells HCT-116, and human embryonic kidney cells HEK 293. HCT-116 cells were grown in Dulbeco's Minimum Essential Medium (DMEM) with 10% fetal bovine serum and 0.1% penicillin/streptomycin as a growth medium for several days at 37° C. under an atmosphere of 5% $CO_2$ to reach confluence. HEK 293 cells were grown in Eagle Minimum Essential Medium (EMEM) with 10% fetal bovine serum and 0.1% penicillin/streptomycin as a growth medium for several days at 37° C. under an atmosphere of 5% $CO_2$ to reach confluence. Each cell type was then plated onto 96-well plates, at 50,000 cells per well at a volume of 150 µl with the respective growth medium. The cells were counted using a hemocytometer and then incubated for 24 hours at 37° C. under an atmosphere of 5% $CO_2$.

The test emulsion was diluted using the growth medium for each cell type, and added into the wells of each test plate to give a final concentration of N-acryloyl ciprofloxacin of 2 mg/ml, 1 mg/ml, 0.5 mg/ml, 0.25 mg/ml, 0.125 mg/ml, and 0.0625 mg/ml within a series. The testing was done in triplicate and one well in each triplicate was left untreated as the negative control for 100% growth. The plates were further incubated and monitored for 48 hours at 37° C. under an atmosphere of 5% $CO_2$. A 5 mg/ml solution of 3-(4,5-dimethyl-2-thiazolyl)-2,5-diphenyltetrazolium bromide (MTT) in sterile phosphate-buffered saline (PBS) was added to give a 10% final concentration in each well. The plates were then further incubated for 4 hours at 37° C. under an atmosphere of 5% $CO_2$ to allow for the formation of the purple crystals of 1-(4,5-dimethylthiazol)2-yl)-3,5-diphenylformazan. The liquid was then aspirated from each well and 100 µl of dimethylsulfoxide (DMSO) was added to each well, and gently shaken for 1 minute to allow for complete dissolution of the crystals. The $IC_{50}$ value for the assay was determined using a BioTek Synergy H1 hybrid plate reader at both 595 nm and 630 nm. The $IC_{50}$ was determined as the well with at least 50% cell viability compared to the untreated control cell with 100% cell growth.

Cytotoxicity Results for Poly(N-Acryloylciprofloxacin) Nanoparticle Emulsions

The observed $IC_{50}$ was 500 µg/ml for both the HCT-116 and HEK-293 cell lines, a 1000-fold difference over the bacterial MIC value for S. aureus and greater than 40,000 for E. coli.

Imaging Nanoparticle Emulsions Using a Scanning Electron Microscope

A sample of poly(N-acryloyl ciprofloxacin) nanoparticle emulsion was prepared for imaging using scanning electron microscope. The samples were initially prepared by lyophilization of the emulsion which resulted in a dry powder that could be added to the sample holder for the scanning electron microscope instrument. The samples were placed onto an aluminum-coated sample holding tape, mounted onto a copper tape, placed onto the scanning electron microscope sample holder. The sample was diluted 1000× with deionized water, and a drop of the diluted emulsion was placed on the conductive aluminum-coated sample holding tape. The sample was placed in the −80° C. freezer for a few hours, then immediately lyophilized to dry the sample right onto the sample holding tape to produce a more even distribution of the material.

In addition, the sample-containing tape was also sputter-coated with gold-palladium in order to increase the conductivity of the resulting sample, thus preventing or reducing the accumulation of electrons on the surface of the sample, and resulting in distortions.

Figure 8:
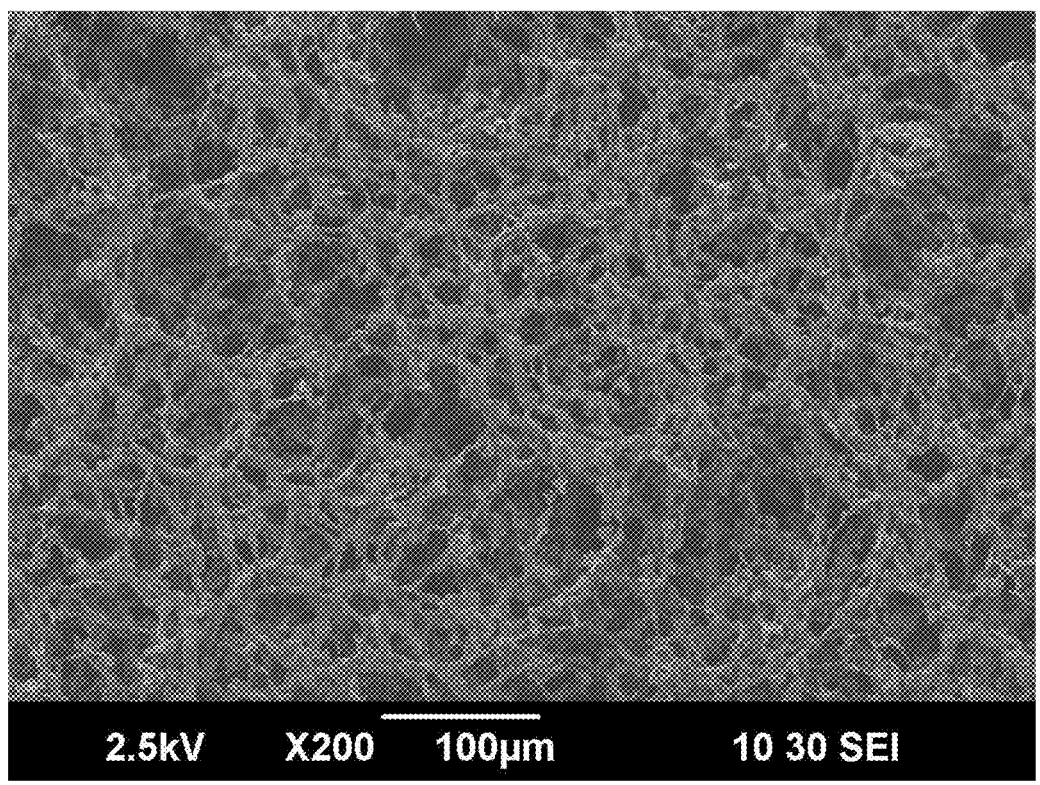
FIG. 8. Scanning electron microscope image of the dried emulsion.
Figure 9:
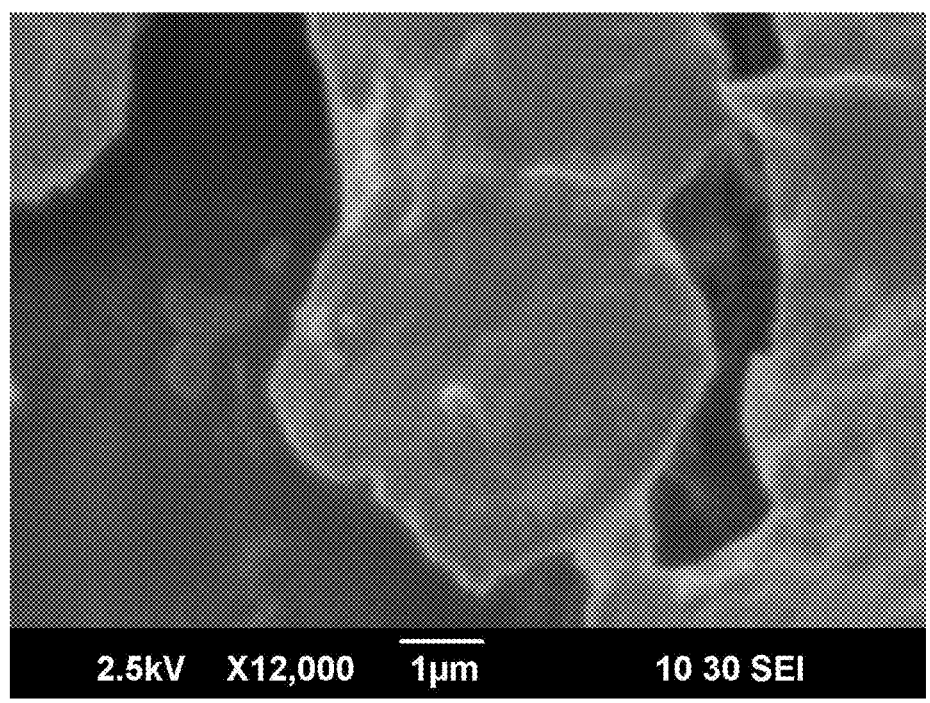
FIG. 9. A zoomed-in SEM image of a potential micelle within the emulsion.

As observed in FIGS. 8 and 9, the images from the scanning electron microscope do not provide clear images of the spheres within the emulsion as were previously observed with butyl acrylate/styrene and poly(menthyl acrylate) emulsions. This was thought to be the result of the material continuing to building up charge on the surface, thus giving a distorted image. Attempts to overcome this effect by ensuring a smooth and conductive surface for the sample holding tape, and sputter-coating with conductive gold-palladium coating, did not improve results. In addition, during the lyophilization process the spheres were dehydrated and deformed, thus resulting in the spheres binding to each other and not remaining separate. This led to the increase of the overall size when viewed from top down with the scanning electron microscope.

Poly(N-acryloylciprofloxacin) nanoparticle emulsions were successfully prepared by modification of the previously reported emulsion polymerization methodology. The main difference with this new method was the need to dissolve the water-insoluble antibacterial agent in an organic solvent to permit more uniform addition into the aqueous solution to form homogeneous emulsions. Dichloromethane provided the best combination of solubilizing the ciprofloxacin monomer and being volatile enough to evaporate from the media during emulsion polymerization at 90° C.

The increased temperature of 90° C. rather than 75° C., an increased stir speed, and the addition of sodium dodecyl sulfate before the organic monomers were added, provided more optimal results. Additionally, it was advantageous to let the reactions run for 48 hours rather than the 6 hours required for the butyl acrylate-styrene co-monomer systems.

These new procedures are required mainly due to the physical properties of the compounds involved, and are pushing the limits and capabilities of the existing available equipment. Higher loading of the drug could perhaps be possible if the mixture could be heated in a pressurized system that would allow for a higher temperature to be achieved without boiling off the water. In addition, a mechanical stirrer able to achieve a higher spin rate that the existing magnetic stir bar method would most likely allow for additional loading of the monomer, since it would provide more uniform distribution of large quantities of the solid monomer.

Lyophilization of the nanoparticle emulsion produced an amorphous powder that could not be reformulated to its original emulsified state through addition of water. Moreover, the resulting powder remained insoluble in organic solvents including methanol, ethanol, dichloromethane, hexane, acetone, ethyl acetate, and dimethylformamide. Extraction of the solid material with methanol, ethanol, dichloromethane, hexane, acetone, or ethyl acetate failed to show any trace of unreacted N-acryloylciprofloxacin upon evaporation and analysis by proton NMR spectroscopy. This confirms that the polymerization is complete, and thus all of the N-acryloylciprofloxacin is incorporated into the framework of the nanoparticle. Attempts to perform the emulsion polymerization procedure on the free ciprofloxacin instead of the N-acryloyl derivative led to a bilayer mixture, not an emulsion, with the layers separating within seconds after stirring was stopped. Additionally, the same procedure was attempted using N-acetyl ciprofloxacin as an analog similar in structure but without the requisite olefin. Once again, only an unstable mixture was formed, which separated into layers with a few seconds after stirring was stopped. Therefore, the acryloyl group is a prerequisite for emulsification and subsequent nanoparticle formation.

This Example provides an aqueous nanoparticle polymer emulsion being formed from a monomer that is the antibiotic agent itself. The emulsion is formed via a one pot reaction in water and the final antibiotic polymer is suspended in water. The emulsified nano-cipro particles are antimicrobially-active towards gram positive *S. aureus* and gram negative *E. coli*.

The methods and nanoparticle emulsions described herein can be used to produce other emulsions containing other antibiotics including water-insoluble antibiotics for delivery and effective treatment of drug-resistant bacterial infections.

All patents, patent applications, provisional applications, and publications referred to or cited herein are incorporated by reference in their entirety, including all figures and tables, to the extent they are not inconsistent with the explicit teachings of this specification.

REFERENCES

1) Turos, E., Reddy, G. S. K., Greenhalgh, K., Ramaraju, P., Abeylath, S. C., Jang, S., et al. Penicillin-bound polyacrylate nanoparticles: Restoring the activity of β-lactam antibiotics against MRSA. Bioorg. Med. Chem. Lett. 2007; 17:3468-72.
2) Turos, E., Shim, J. Y., Wang, Y., Greenhalgh, K., Reddy, G. S., Dickey, S., et al. Antibiotic-conjugated polyacrylate nanoparticles: New opportunities for development of anti-MRSA agents. Bioorg. Med. Chem. Lett. 2007; 17:53-6.
3) Greenhalgh, K., Turos, E. In vivo studies of polyacrylate nanoparticle emulsions for topical and systemic applications. Nanomedicine: Nanotechnology, Biology, and Medicine, 2009; 5:46-54.
4) Garay-Jimenez, J. C., Turos, E. A convenient method to prepare emulsified polyacrylate nanoparticles from powders for drug delivery applications. Bioorg. Med. Chem. Lett. 2011; 21:4589-91.
5) Abeylath, S., Turos, E. Glycosylated polyacrylate nanoparticles by emulsion polymerization. Carb. Polym. 2007; 70:32-7.
6) Abeylath, S., Turos, E., Dickey, S., Lim, D. V. Novel carbohydrated nanoparticle antibiotics for MRSA and Bacillus anthracis. Bioorg. Med. Chem. 2008; 16:2412-8.
7) Labruère, R., Turos, E. Attenuating the size and molecular carrier capabilities of polyacrylate nanoparticles by a hydrophobic fluorine effect. Bioorg. Med. Chem. 2012; 20:5042-5.
8) Garay, J., Gergeres, D., Young, A., Dickey, S., Lim, D., Turos, E. Physical properties and biological activity of poly(butyl acrylate-styrene) nanoparticle emulsions prepared with conventional and polymerizable surfactants. Nanomedicine. 2009; 5:443-51.
9) Abeylath, S. C., Turos, E. Nanobiotics to combat bacterial drug resistance. In Antibiotic Resistance: Causes and Risk Factors, Mechanisms and Alternatives. Adriel R. Bonilla and Kaden P. Muniz (eds.), Nova Science Publishers. 2009; 425-65.
10) Cormier, R., Burda, W., Harrington, L., Edlinger, J., Kodigepalli, K., Thomas, J., Kapolka, R., Roma, G., Anderson, B., Turos, E., Shaw, L., Studies on the antimicrobial properties of N-acylated ciprofloxacins. Bioorg. Med. Chem. Lett. 2012; 22:6513-20.
11) Thamizharasi, S., Vasantha, J. Synthesis, characterization and pharmacologically active sulfamethoxazole polymers. Eur. Polym. J. 2002; 38: 551-9.
12) Moon, W. S., Chung, K., H. Antimicrobial effect of monomers and polymers with azole moieties. J. Appl. Polym. Sci. 2003; 90:2933-7.
13) Kanazawa, A., Ikeda, T. J. Antibacterial activity of polymeric sulfonium salts. Polym. Sci., Part A: Polym. Chem. 1993; 31:2873-6.

We claim:

1. A homopolymer consisting of a polymerized acrylolated drug monomer, wherein the acrylolated drug monomer is an antibiotic selected from a β-lactam or a fluoroquinolone.

2. A nanoparticle comprising the homopolymer of claim 1.

3. The homopolymer of claim 1, wherein the β-lactam is benzylpenicillin, benzathine benzylpenicillin, procaine benzylpenicillin, phenoxymethylpenicillin (V), propicillin, pheneticillin, azidocillin, clometocillin, penamecillin, cloxacillin, dicloxacillin, flucloxacillin, oxacillin, nafcillin, methicillin, amoxicillin, ampicillin, pivampicillin, hetacillin, bacampicillin, metampicillin, talampicillin, epicillin, ticarcillin, carbenicillin, carindacillin, temocillin, piperacillin, azlocillin, mezlocillin, mecillinam, pivmecillinam, sulbenicillin, faropenem, ritipenem, ertapenem, antipseudomonal, doripenem, imipenem, meropenem, biapenem, panipenem, cefazolin, cefalexin, cefadroxil, cefapirin, cefazedone, cefazaflur, cefradine, cefroxadine, ceftezole, cefaloglycin, cefacetrile, cefalonium, cfaloridine, cefalotin, cefatrizine, cefaclor, cefotetan, cephamycin, cefoxitin, cefprozil, cefuroxime, cefuroxime axetil, cefamandole, cefminox, cefonicid, ceforanide, cefotiam, cefbuperazone, cefuzonam, cefmetazole, carbacephem, loracarbef, cefixime, ceftriaxone, antipseudomonal, ceftazidime, cefoperazone, cefdinir, cefcapene, cefdaloxime, ceftizoxime, cefmenoxime, cefotaxime, cefpiramide, cefpodoxime, ceftibuten, cefditoren, cefetamet, cefodizime, cefpimizole, cefsulodin, cefteram, ceftiolene, oxacephem, flomoxef, latamoxef, cefepime, cefozopran, cefpirome, cefquinome, ceftaroline fosamil, ceftolozane, ceftobiprole, ceftiofur, cefquinome, cefovecin, aztreonam, tigemonam, carumonam, or nocardicin A.

4. The homopolymer of claim 1, wherein the fluoroquinolone is enoxacin, ciprofloxacin, norfloxacin, ofloxacin, levofloxacin, trovafloxacin, gatifloxacin, or moxifloxacin.

5. The nanoparticle of claim 2, having a size of between 600 nm to 1000 nm.

6. The nanoparticle of claim 2, further comprising a detergent.

7. The nanoparticle of claim 6, wherein the detergent is sodium dodecyl sulfate, cetyltrimethylammonium bromide, 3-(N,N-dimethylmyristylammonio)propanosulfonate, dedecanoic acid 2-(2-hydroxyethoxy)ethyl ester, sodium 11-(acrylolyloxyundecan-1-yl) sulfate, N-(11-Acryloyloxyundecyl)-N-(2-hydroxyethyl)-N,N-dimethylammoniuim bromide, N-(11-Acryloyloxyundecyl)-N,N-dimethyl-N-ethylammonium bromide, 3-[N,N-Diethyl-N-(3-sulfopropyl) ammonio]acrylate, 2(2-Acryloyloxyethoxy)ethyl dodecanoate, or any mixture thereof.

* * * * *